US010864459B2

(12) United States Patent
Wagner et al.

(10) Patent No.: US 10,864,459 B2
(45) Date of Patent: *Dec. 15, 2020

(54) METHODS TO PRODUCE CANNABINOID PRODUCTS FROM DECARBOXYLATED CANNABINOID EXTRACTS

(71) Applicant: Natural Extraction Systems, LLC, Boulder, CO (US)

(72) Inventors: Robert C. Wagner, Boulder, CO (US); C. Russell Thomas, Boulder, CO (US); Douglas G. Metcalf, Erie, CO (US)

(73) Assignee: Natural Extraction Systems, LLC, Boulder, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/683,055

(22) Filed: Nov. 13, 2019

(65) Prior Publication Data

US 2020/0179471 A1 Jun. 11, 2020

Related U.S. Application Data

(62) Division of application No. 16/680,365, filed on Nov. 11, 2019, now Pat. No. 10,610,805.

(60) Provisional application No. 62/777,608, filed on Dec. 10, 2018, provisional application No. 62/780,181, filed on Dec. 14, 2018, provisional application No. 62/787,724, filed on Jan. 2, 2019, provisional application No. 62/803,412, filed on Feb. 8, 2019, provisional application No. 62/812,852, filed on Mar. 1, 2019, provisional application No. 62/818,695, filed on Mar. 14, 2019, provisional application No. 62/821,971, filed on Mar. 21, 2019, provisional application No. 62/832,009, filed on Apr. 10, 2019, provisional application No. 62/839,569, filed on Apr.

(Continued)

(51) Int. Cl.
| | | |
|---|---|---|
| C07C 29/84 | (2006.01) | |
| C07D 311/00 | (2006.01) | |
| A61K 31/00 | (2006.01) | |
| B01D 11/04 | (2006.01) | |
| C07D 311/80 | (2006.01) | |
| A61K 31/015 | (2006.01) | |
| A61K 31/05 | (2006.01) | |
| A61K 31/352 | (2006.01) | |
| A61K 36/185 | (2006.01) | |

(52) U.S. Cl.
CPC ........ *B01D 11/0492* (2013.01); *A61K 31/015* (2013.01); *A61K 31/05* (2013.01); *A61K 31/352* (2013.01); *A61K 36/185* (2013.01); *C07C 29/84* (2013.01); *C07D 311/80* (2013.01); *A61K 2236/331* (2013.01); *A61K 2236/39* (2013.01); *A61K 2236/51* (2013.01); *A61K 2236/53* (2013.01); *A61K 2236/55* (2013.01)

(58) Field of Classification Search
CPC ....... C07C 29/84; C07D 311/20; A61K 31/05; A61K 31/352
See application file for complete search history.

(56) References Cited

U.S. PATENT DOCUMENTS

2018/0360757 A1* 12/2018 Doroudian ........... A61K 31/047

FOREIGN PATENT DOCUMENTS

EP 3459536 A1 * 3/2019 ............. A61K 31/05

* cited by examiner

*Primary Examiner* — Sikarl A Witherspoon
(74) *Attorney, Agent, or Firm* — Douglas G. Metcalf

(57) ABSTRACT

Various aspects of this patent application relate to methods to separate a cannabinoid molecule from other molecules of a decarboxylated cannabinoid extract.

20 Claims, 1 Drawing Sheet

Related U.S. Application Data

26, 2019, provisional application No. 62/860,218, filed on Jun. 11, 2019, provisional application No. 62/925,203, filed on Oct. 23, 2019, provisional application No. 62/933,742, filed on Nov. 11, 2019.

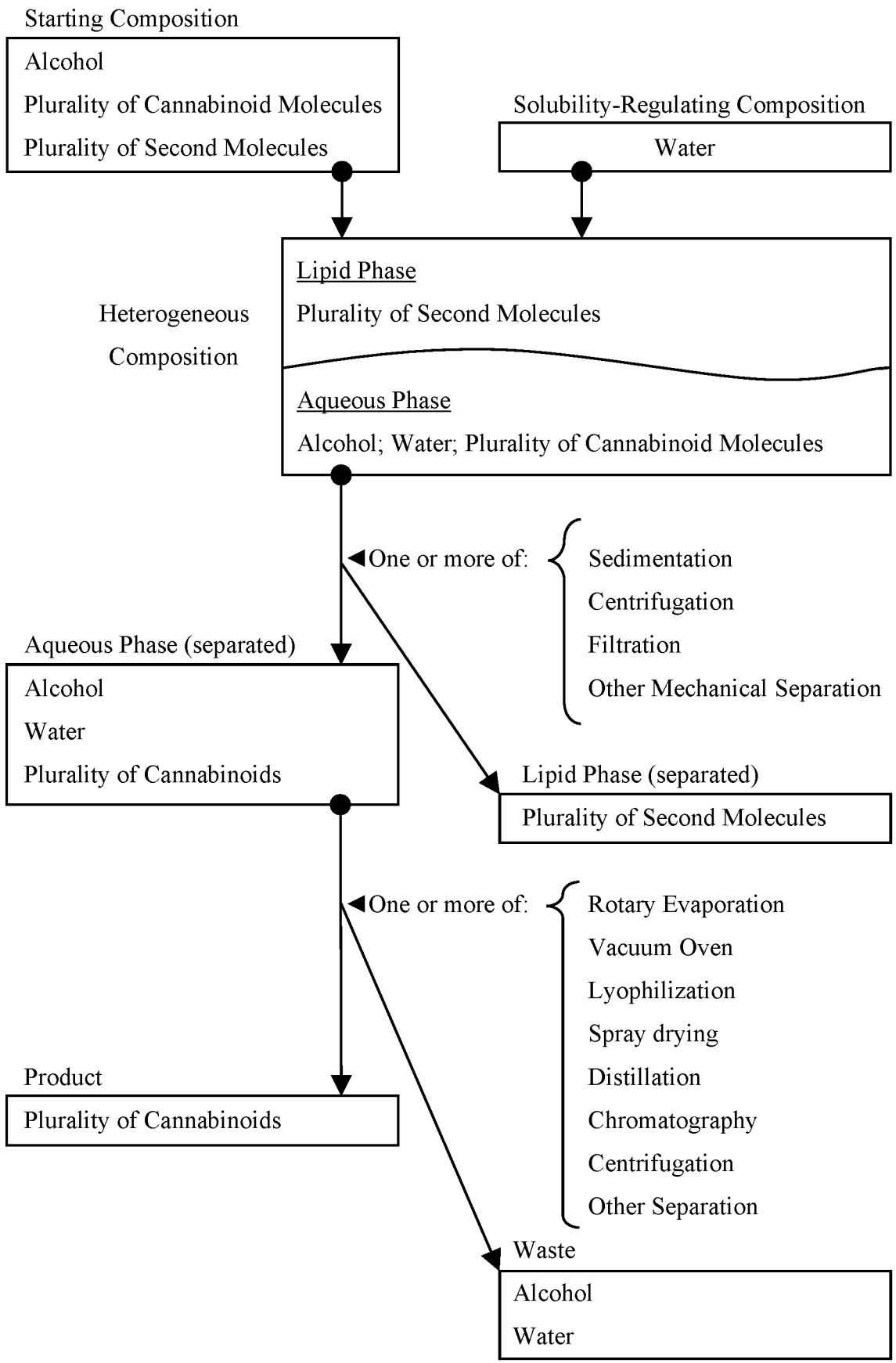

METHODS TO PRODUCE CANNABINOID PRODUCTS FROM DECARBOXYLATED CANNABINOID EXTRACTS

RELATED PATENT APPLICATIONS

This patent application is a division of U.S. patent application Ser. No. 16/680,365, filed Nov. 11, 2019, and this patent application claims the benefit under 35 U.S.C. § 120 of Ser. No. 16/680,365 and of the following U.S. provisional patent applications: U.S. 62/777,608, filed Dec. 10, 2018; U.S. 62/780,181, filed Dec. 14, 2018; U.S. 62/787,724, filed Jan. 2, 2019; U.S. 62/803,412, filed Feb. 8, 2019; U.S. 62/812,852, filed Mar. 1, 2019; U.S. 62/818,695, filed Mar. 14, 2019; U.S. 62/821,971, filed Mar. 21, 2019; U.S. 62/832,009, filed Apr. 10, 2019; U.S. 62/839,569, filed Apr. 26, 2019; U.S. 62/860,218, filed Jun. 11, 2019; and U.S. 62/925,203, filed Oct. 23, 2019, and the contents of each prior-filed application is incorporated by reference in its entirety.

BACKGROUND

Concentrated cannabinoid products are typically produced by extracting lipids from *cannabis*, decarboxylating the cannabinoid carboxylic acids of an extract, and then purifying the decarboxylated cannabinoids. Industrial hemp extracts contain both cannabidiol, which displays significant beneficial pharmacological properties, and tetrahydrocannabinol, which is a regulated psychoactive drug. State-of-the-art techniques to separate cannabidiol from tetrahydrocannabinol to reduce the tetrahydrocannabinol content of cannabidiol products include flash chromatography, high-performance liquid chromatography, centrifugal partition chromatography, and crystallization. These methods generally require hydrocarbon solvents, however, which are both expensive and limit the ability to obtain organic certification on finished consumer products. Separation methods that reduce the need for hydrocarbon solvents and allow organic certification are therefore desirable.

SUMMARY

Various aspects of this patent document relate to methods to separate a cannabinoid molecule from a second molecule of a decarboxylated cannabinoid extract to produce a concentrated cannabinoid product.

BRIEF DESCRIPTION OF THE DRAWING

The FIGURE is a flow chart that depicts an embodiment of this patent document to provide a graphical representation to aid the interpretation of this patent document. The FIGURE shall not be construed to limit either the disclosure of this patent document or any patent claim that matures from this patent document.

DETAILED DESCRIPTION

Various aspects of this patent document relate to methods to separate a cannabinoid molecule from a second molecule. Representative cannabinoids include cannabidiol, cannabidivarin, tetrahydrocannabinol, tetrahydrocannabivarin, cannabigerol, cannabigerovarin, cannabichromene, cannabichromevarin, and cannabinol, which are depicted in Formulas I, II, III, IV, V, VI, VII, VIII, and IX, respectively, and further identified in Table 1.

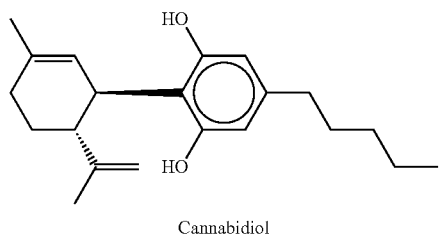

Cannabidiol (I)

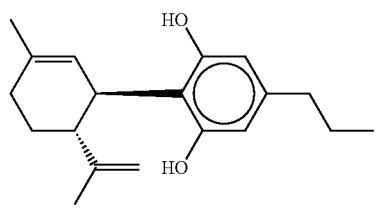

Cannabidivarin (II)

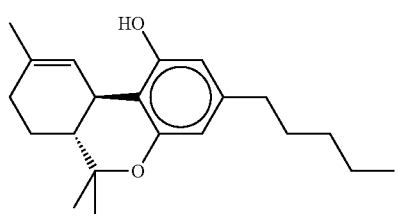

Tetrahydrocannabinol (III)

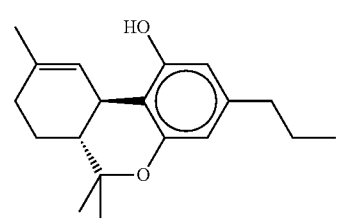

Tetrahydrocannabivarin (IV)

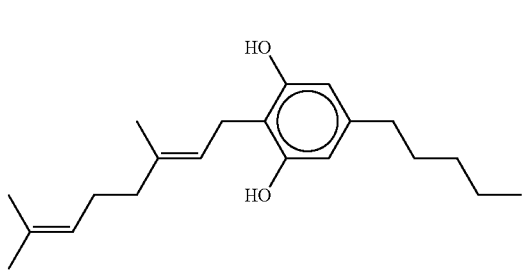

Cannabigerol (V)

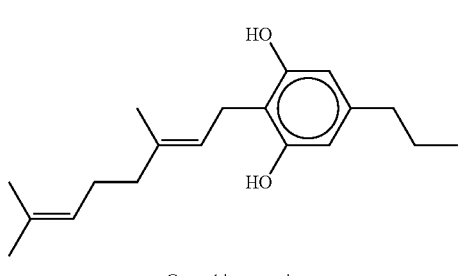

Cannabigerovarin (VI)

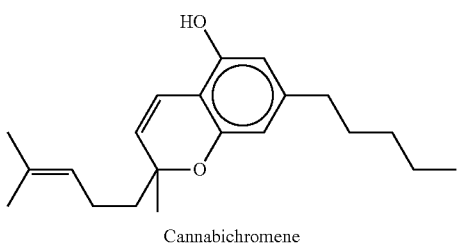

Cannabichromene

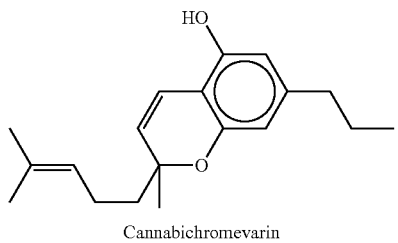

Cannabichromevarin

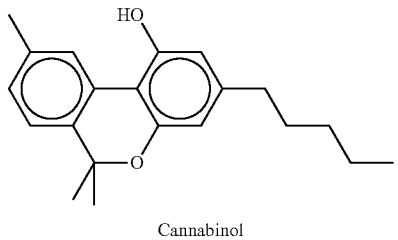

Cannabinol

TABLE 1

Names of the Cannabinoids of Formulas I-IX

| Formula | Common Name | Chemical Name |
| --- | --- | --- |
| I | Cannabidiol | 2-[(1R,6R)-6-isopropenyl-3-methylcyclohex-2-en-1-yl]-5-pentylbenzene-1,3-diol |
| II | Cannabidivarin | 2-[(1R,6R)-6-isopropenyl-3-methylcyclohex-2-en-1-yl]-5-propylbenzene-1,3-diol |
| III | Tetrahydrocannabinol | (6aR,10aR)-6,6,9-trimethyl-3-pentyl-6a,7,8,10a-tetrahydro-6H-benzo[c]chromen-1-ol |
| IV | Tetrahydrocannabivarin | (6aR,10aR)-6,6,9-trimethyl-3-propyl-6a,7,8,10a-tetrahydro-6H-benzo[c]chromen-1-ol |
| V | Cannabigerol | 2-[(2E)-3,7-dimethylocta-2,6-dien-1-yl]-5-pentylbenzene-1,3-diol |
| VI | Cannabigerovarin | 2-[(2E)-3,7-dimethylocta-2,6-dien-1-yl]-5-propylbenzene-1,3-diol |
| VII | Cannabichromene | 2-methyl-2-(4-methylpent-3-en-1-yl)-5-hydroxy-7-pentyl-2H-1-benzopyran* |
| VIII | Cannabichromevarin | 2-methyl-2-(4-methylpent-3-en-1-yl)-5-hydroxy-7-propyl-2H-1-benzopyran* |
| IX | Cannabinol | 6,6,9-trimethyl-3-pentyl-6H-benzo[c]chromen-1-ol |

*Each of cannabichromene and cannabichromevarin have two stereoisomers; the lack of stereochemical identifiers in the chemical names of cannabichromene and cannabichromevarin indicate that the chemical name refers to either one or both of the stereoisomers of cannabichromene or cannabichromevarin, respectively.

Various aspects of this patent document relate to a method to produce a cannabinoid glass from a decarboxylated cannabinoid extract. The cannabinoids of a cannabinoid glass are generally bioavailable, and thus, cannabinoid glasses can be directly added to products for oral consumption.

Various aspects of this patent document relate to a method to produce cannabinoid crystals from a decarboxylated cannabinoid extract. Cannabinoid crystals can be used in the development of cannabinoid products, but cannabinoid crystals generally lack bioavailability because humans generally cannot melt or dissolve cannabinoid crystals.

Various aspects of this patent document relate to a method to produce a cannabinoid oil from a decarboxylated cannabinoid extract. Cannabinoid oils can be used, for example, in vape products, but many cannabinoid oils spontaneously crystallize, which produces local variations in concentration and limits the utility of an oil as an ingredient.

Various aspects of this patent document relate to a method to produce a supercooled cannabinoid oil from a decarboxylated cannabinoid extract. Cannabinoid oils can be used, for example, in vape products, but supercooled cannabinoid oils can spontaneously crystallize, which produces local variations in concentration and limits the utility of a supercooled oil as an ingredient.

In some embodiments, a method comprises combining (a) a starting composition comprising a decarboxylated cannabinoid extract and (b) a solubility-regulating composition to produce a heterogeneous composition, in which the starting composition comprises an alcohol, a cannabinoid molecule, and a second molecule; the alcohol is a solvent of the starting composition; the cannabinoid molecule is a solute that is dissolved in the alcohol of the starting composition; the second molecule is a solute that is dissolved in the alcohol of the starting composition; the solubility-regulating composition comprises water; the heterogeneous composition comprises an aqueous phase and a lipid phase; the aqueous phase of the heterogeneous composition comprises at least 95 percent of the water of the heterogeneous composition; the aqueous phase of the heterogeneous composition comprises at least 65 percent of the alcohol of the heterogeneous composition (such as at least 95 percent of the alcohol of the heterogeneous composition); the second molecule has a solubility in the aqueous phase that is less than 10 grams per liter; the lipid phase comprises greater than 65 percent of the second molecule of the heterogeneous composition; the cannabinoid molecule has a solubility in the aqueous phase that is greater than 10 grams per liter; the aqueous phase comprises greater than 65 percent of the cannabinoid molecule of the heterogeneous composition; the method comprises separating the aqueous phase and the lipid phase to separate the cannabinoid molecule and the second molecule; the method comprises separating the cannabinoid molecule from both (a) at least 95 percent of the water of the aqueous phase and (b) at least 95 percent of the alcohol of the aqueous phase to produce a product; the product comprises the molecules of the aqueous phase that are separated from (a) the at least 95 percent of the water of the aqueous phase and (b) the at least 95 percent of the alcohol of the aqueous phase; the product lacks the second molecule at a concentration greater than 0.3 percent by mass; and the product comprises crystals, a glass, or an oil.

In some embodiments, a method comprises combining (a) a starting composition comprising a decarboxylated cannabinoid extract and (b) a solubility-regulating composition to produce a heterogeneous composition, in which the starting composition comprises an alcohol, a plurality of cannabinoid molecules, and a plurality of second molecules; the alcohol is a solvent of the starting composition; each cannabinoid molecule of the plurality of cannabinoid molecules is a solute that is dissolved in the alcohol of the starting composition; each second molecule of the plurality of second molecules is a solute that is dissolved in the alcohol of the starting composition; the solubility-regulating composition comprises water; the heterogeneous composition comprises an aqueous phase and a lipid phase; the aqueous phase of the heterogeneous composition comprises at least 95 percent of the water of the heterogeneous composition; the aqueous phase of the heterogeneous composition comprises at least 65 percent of the alcohol of the heterogeneous composition (such as at least 95 percent of the alcohol of the heterogeneous composition); each second molecule of the plurality of second molecules has a solubility in the aqueous phase that is less than 10 grams per liter; the lipid phase comprises greater than 65 percent by mass of each second molecule of the plurality of second molecules of the heterogeneous composition; each cannabinoid molecule of the plurality of cannabinoid molecules has a solubility in the aqueous phase that is greater than 10 grams per liter; the aqueous phase comprises greater than 65 percent by mass of each cannabinoid molecule of the plurality of cannabinoid molecules of the heterogeneous composition; the method comprises separating the aqueous phase and the lipid phase to separate (a) each cannabinoid molecule of the plurality of cannabinoid molecules and (b) each second molecule of the plurality of second molecules; the method comprises separating the cannabinoid molecules of the plurality of cannabinoid molecules from both (a) at least 95 percent of the water of the aqueous phase and (b) at least 95 percent of the alcohol of the aqueous phase to produce a product; the product comprises the molecules of the aqueous phase that are separated from (a) the at least 95 percent of the water of the aqueous phase and (b) the at least 95 percent of the alcohol of the aqueous phase; the product lacks each second molecule of the plurality of second molecules at a concentration greater than 0.3 percent by mass; and the product comprises crystals, a glass, or an oil.

In some embodiments, the decarboxylated cannabinoid extract is a decarboxylated *cannabis* extract. In some specific embodiments, the decarboxylated cannabinoid extract is a decarboxylated full spectrum industrial hemp extract, a decarboxylated broad spectrum industrial hemp extract, or a decarboxylated industrial hemp distillate.

In some embodiments, the decarboxylated cannabinoid extract is derived from an organism other than *cannabis* such as a bacterium, yeast, cell line, or plant that has been genetically modified to biosynthetically produce a cannabinoid.

In some embodiments, the method comprises heating a cannabinoid extract to decarboxylate the cannabinoid extract and produce the decarboxylated cannabinoid extract. In some specific embodiments, the method comprises heating a *cannabis* extract to decarboxylate the *cannabis* extract and produce the decarboxylated cannabinoid extract. In some very specific embodiments, the method comprises heating an industrial hemp extract to decarboxylate the industrial hemp extract and produce the decarboxylated cannabinoid extract.

In some embodiments, the method comprises dissolving the decarboxylated cannabinoid extract in the alcohol to produce the starting composition.

In some embodiments, the alcohol is selected from methanol, ethanol, 1-propanol, 2-propanol, propane-1,2-diol, and propane-1,3-diol. In some specific embodiments, the alcohol is ethanol.

In some embodiments, the cannabinoid molecule is selected from cannabidiol, cannabidivarin, cannabigerol, and cannabigerovarin. In some specific embodiments, the cannabinoid molecule is cannabidiol or cannabidivarin. In some very specific embodiments, the cannabinoid molecule is cannabidiol.

In some embodiments, the cannabinoid molecules of the plurality of cannabinoid molecules comprise two, three, or each of cannabidiol, cannabidivarin, cannabigerol, and cannabigerovarin.

In some embodiments, the second molecule is selected from tetrahydrocannabinol, tetrahydrocannabivarin, cannabichromene, cannabichromevarin, cannabinol, beta-caryophyllene, bisabolol, eucalyptol, guaiol, humulene, limonene, myrcene, nerolidol, ocimene, pinene, terpinolene, and linalool. In some specific embodiments, the second molecule is selected from tetrahydrocannabinol, tetrahydrocannabivarin, and beta-caryophyllene. In some very specific embodiments, the second molecule is tetrahydrocannabinol.

In some embodiments, the cannabinoid molecule is cannabidiol, and the second molecule is tetrahydrocannabinol.

In some embodiments, the cannabinoid molecule is cannabidivarin, and the second molecule is tetrahydrocannabivarin.

In some embodiments, the cannabinoid molecule is cannabigerol, and the second molecule is beta-caryophyllene.

In some embodiments, the plurality of cannabinoid molecules comprises cannabidiol and cannabigerol, and the plurality of second molecules comprises tetrahydrocannabinol and cannabichromene.

In some embodiments, the plurality of cannabinoid molecules comprises cannabidivarin and cannabigerovarin, and the plurality of second molecules comprises tetrahydrocannabivarin and cannabichromevarin.

In some embodiments, the solubility-regulating composition comprises water at a concentration of at least 50 percent by mass. In some specific embodiments, the solubility-regulating composition comprises water at a concentration of at least 65 percent by mass. In some specific embodiments, the solubility-regulating composition comprises water at a concentration of at least 90 percent by mass.

In some embodiments, separating the aqueous phase and the lipid phase to separate the cannabinoid molecule and the second molecule comprises centrifuging the heterogeneous composition. In some embodiments, separating the aqueous phase and the lipid phase to separate the cannabinoid molecule and the second molecule comprises filtering the heterogeneous composition. In some embodiments, separating the aqueous phase and the lipid phase to separate the cannabinoid molecule and the second molecule comprises gravity-assisted sedimentation of the heterogeneous composition.

The term "sedimentation" refers to the spontaneous separation of a lipid phase and an aqueous phase based on density and irrespective of both the state(s) of matter of the lipid phase and the relative densities of the lipid phase and the aqueous phase.

The terms "separate," "separated," "separating," and "separation" refer to both theoretical separations that are 100 percent complete and real-world separations that are less than 100 percent complete.

In some embodiments, separating the cannabinoid molecule from both (a) the at least 95 percent of the water of the aqueous phase and (b) the at least 95 percent of the alcohol of the aqueous phase comprises (i) vaporizing the at least 95 percent of the water to produce water vapor, (ii) vaporizing the at least 95 percent of the alcohol to produce alcohol vapor, and (iii) removing both the water vapor and the alcohol vapor from the aqueous phase using a vacuum, in which the vaporizing and removing are performed under conditions that do not vaporize and remove the cannabinoid molecule of the aqueous phase from the aqueous phase; and the product consists of the portion of the aqueous phase that is not both vaporized and removed from the aqueous phase.

In some embodiments, separating the cannabinoid molecule from both (a) the at least 95 percent of the water of the aqueous phase and (b) the at least 95 percent of the alcohol of the aqueous phase comprises removing (a) the at least 95 percent of the water of the aqueous phase and (b) the at least 95 percent of the alcohol of the aqueous phase under vacuum either in a rotary evaporator, in a vacuum oven, or by lyophilization.

In some embodiments, separating the cannabinoid molecule from both (a) the at least 95 percent of the water of the aqueous phase and (b) the at least 95 percent of the alcohol of the aqueous phase comprises spray drying the aqueous phase.

In some embodiments, separating the cannabinoid molecules of the plurality of cannabinoid molecules from both (a) the at least 95 percent of the water of the aqueous phase and (b) the at least 95 percent of the alcohol of the aqueous phase comprises (i) vaporizing the at least 95 percent of the water to produce water vapor, (ii) vaporizing the at least 95 percent of the alcohol to produce alcohol vapor, and (iii) removing both the water vapor and the alcohol vapor from the aqueous phase using a vacuum, in which the vaporizing and removing are performed under conditions that do not vaporize and remove the cannabinoid molecules of the plurality of cannabinoid molecules of the aqueous phase from the aqueous phase; and the product consists of the portion of the aqueous phase that is not both vaporized and removed from the aqueous phase.

In some embodiments, separating the cannabinoid molecules of the plurality of cannabinoid molecules from both (a) the at least 95 percent of the water of the aqueous phase and (b) the at least 95 percent of the alcohol of the aqueous phase comprises removing (a) the at least 95 percent of the water of the aqueous phase and (b) the at least 95 percent of the alcohol of the aqueous phase under vacuum either in a rotary evaporator, in a vacuum oven, or by lyophilization.

In some embodiments, separating the cannabinoid molecules of the plurality of cannabinoid molecules from both (a) the at least 95 percent of the water of the aqueous phase and (b) the at least 95 percent of the alcohol of the aqueous phase comprises spray drying the aqueous phase.

In some embodiments, separating the cannabinoid molecule from both (a) the at least 95 percent of the water of the aqueous phase and (b) the at least 95 percent of the alcohol of the aqueous phase comprises combining the aqueous phase and a second solubility-regulating composition to (i) drive a portion of the cannabinoid molecule of the aqueous phase out of the aqueous phase and (ii) produce a second heterogeneous composition, in which the second heterogeneous composition comprises a residual aqueous phase and a second lipid phase; the residual aqueous phase is a liquid; the residual aqueous phase comprises greater than 65 percent of the alcohol of the second heterogeneous composition (such as at least 95 percent of the alcohol of the second heterogeneous composition); the residual aqueous phase comprises greater than 95 percent of the water of the second heterogeneous composition; the cannabinoid molecule of the second heterogeneous composition has a solubility in the residual aqueous phase that is less than 10 grams per liter; the second lipid phase comprises greater than 80 percent of the cannabinoid molecule of the second heterogeneous composition; the separation of the cannabinoid molecule from both (a) the at least 95 percent of the water of the aqueous phase and (b) the at least 95 percent of the alcohol of the aqueous phase further comprises mechanically separating the residual aqueous phase of the second heterogeneous composition from the second lipid phase of the second heterogeneous composition; and the product consists essentially of the portion of the second lipid phase that is mechanically separated from the residual aqueous phase.

In some embodiments, separating the cannabinoid molecules of the plurality of cannabinoid molecules from both (a) the at least 95 percent of the water of the aqueous phase and (b) the at least 95 percent of the alcohol of the aqueous phase comprises combining the aqueous phase and a second solubility-regulating composition to (i) drive a portion of the cannabinoid molecules of the plurality of cannabinoid molecules of the aqueous phase out of the aqueous phase and (ii) produce a second heterogeneous composition, in which the second heterogeneous composition comprises a residual aqueous phase and a second lipid phase; the residual aqueous phase is a liquid; the residual aqueous phase comprises greater than 65 percent of the alcohol of the second heterogeneous composition (such as at least 95 percent of the alcohol of the second heterogeneous composition); the residual aqueous phase comprises greater than 95 percent of the water of the second heterogeneous composition; each cannabinoid molecule of the plurality of cannabinoid molecules of the second heterogeneous composition has a solubility in the residual aqueous phase that is less than 10 grams per liter; the second lipid phase comprises greater than 80 percent by mass of each cannabinoid molecule of the plurality of cannabinoid molecules of the second heterogeneous composition; the separation of the cannabinoid molecules of the plurality of cannabinoid molecules from both (a) the at least 95 percent of the water of the aqueous phase and (b) the at least 95 percent of the alcohol of the aqueous phase further comprises mechanically separating the residual aqueous phase of the second heterogeneous composition from the second lipid phase of the second heterogeneous composition; and the product consists essentially of the portion of the second lipid phase that is mechanically separated from the residual aqueous phase.

In some embodiments, the crystals, the glass, or the oil comprises the cannabinoid molecule at a concentration of greater than 50 percent by mass.

In some embodiments, the crystals, the glass, or the oil comprises greater than 50 percent of the cannabinoid molecule of the product.

In some embodiments, the crystals, the glass, or the oil comprises a cannabinoid molecule of the plurality of cannabinoid molecules at a concentration of greater than 50 percent by mass.

In some embodiments, the crystals, the glass, or the oil comprises greater than 50 percent by mass of a cannabinoid molecule of the plurality of cannabinoid molecules.

In some embodiments, the cannabinoid molecule has a freezing point; the product comprises a glass; the glass comprises greater than 50 percent of the cannabinoid molecule of the product; the glass comprises the cannabinoid molecule at a concentration greater than 50 percent by mass; the glass has a glass-transition temperature that is less than the freezing point of cannabinoid molecule; the glass lacks a freezing point; and the glass lacks a melting point.

In some embodiments, the product comprises a glass; the glass comprises an abundant cannabinoid molecule of the plurality of cannabinoid molecules at a concentration greater than 50 percent by mass; the glass comprises greater than 50 percent of the abundant cannabinoid molecule of the product; the abundant cannabinoid molecule has a freezing point; the glass has a glass-transition temperature that is less than the freezing point of the abundant cannabinoid molecule; the glass lacks a freezing point; and the glass lacks a melting point.

In some embodiments, the product comprises crystals; the crystals comprise greater than 50 percent of the cannabinoid molecule of the product; the crystals comprise the cannabinoid molecule at a concentration greater than 50 percent by mass; the crystals have a melting point; and the crystals lack a glass-transition temperature.

In some embodiments, the product comprises crystals; the crystals comprise an abundant cannabinoid molecule of the plurality of cannabinoid molecules at a concentration greater than 50 percent by mass; the crystals comprise greater than 50 percent of the abundant cannabinoid molecule of the product; the crystals have a melting point; and the crystals lack a glass-transition temperature.

In some embodiments, the product is a powder. In some specific embodiments, the product is a microcrystalline powder. In some very specific embodiments, the product is a microcrystalline powder, and the microcrystalline powder consists of crystals.

In some embodiments, the product comprises an oil; the oil comprises greater than 50 percent of the cannabinoid molecule of the product; and the oil comprises the cannabinoid molecule at a concentration greater than 50 percent by mass. In some specific embodiments, the product comprises an oil; the oil comprises greater than 50 percent of the cannabinoid molecule of the product; the oil comprises the cannabinoid molecule at a concentration greater than 50 percent by mass; the oil is a supercooled liquid; the oil has a freezing point; and the oil lacks a glass-transition temperature.

In some embodiments, the product comprises an oil; the oil comprises an abundant cannabinoid molecule of the plurality of cannabinoid molecules at a concentration greater than 50 percent by mass; and the oil comprises greater than 50 percent of the abundant cannabinoid molecule of the product. In some specific embodiments, the product comprises an oil; the oil comprises an abundant cannabinoid molecule of the plurality of cannabinoid molecules at a concentration greater than 50 percent by mass; the oil comprises greater than 50 percent of the abundant cannabinoid molecule of the product; the oil is a supercooled liquid; the oil has a freezing point; and the oil lacks a glass-transition temperature.

In some embodiments, the alcohol is ethanol; the starting composition has an ethoxide concentration; the aqueous phase has an ethoxide concentration; and combining (a) the starting composition and (b) the solubility-regulating composition decreases the ethoxide concentration of the starting composition to arrive at the ethoxide concentration of the aqueous phase. In some specific embodiments, the alcohol is ethanol; the starting composition has an ethoxide concentration; the aqueous phase has an ethoxide concentration; and combining (a) the starting composition and (b) the solubility-regulating composition decreases the ethoxide concentration of the starting composition to arrive at the ethoxide concentration of the aqueous phase such that the ethoxide concentration of the aqueous phase is at least 0.2 nanomolar less than the ethoxide concentration of the starting composition. In some specific embodiments, the alcohol is ethanol; the starting composition has an ethoxide concentration; the aqueous phase has an ethoxide concentration; and combining (a) the starting composition and (b) the solubility-regulating composition decreases the ethoxide concentration of the starting composition to arrive at the ethoxide concentration such that the ethoxide concentration of the aqueous phase is less than 95 percent of the ethoxide concentration of the starting composition. For example, the starting composition may have an ethoxide concentration of about 50 nanomolar, and the aqueous phase may have an ethoxide concentration of about 40 nanomolar, which is both at least 0.2 nanomolar less than the ethoxide concentration of the starting composition and less than 95 percent of the ethoxide concentration of the starting composition.

Various combinations of the features disclosed in this patent document will be evident to those of ordinary skill, and these combinations are expressly contemplated. This patent document discloses each linguistic and grammatical combination of different features disclosed anywhere in the patent document as though any specific combination were disclosed in the same sentence. The language and grammar of this patent document are intentionally selected to explicitly clarify the combinations contemplated such that, for example, methods that feature the genus "alcohol" are combinable with every "ethanol" embodiment and every "ethoxide" embodiment described in this patent document.

The words "comprising," "comprises," and "comprise" refer to open-ended sets. For example, a composition comprising water can also comprise ions that are dissolved in the water.

The phrases "consisting of," "consists of," and "consist of" refer to closed sets. For example, a product that consists of a portion of an aqueous phase that is not both vaporized and removed from the aqueous phase cannot also comprise any molecule that is both vaporized and removed, although the product may comprise a molecule of the type that is both vaporized and removed, for example, when a separation is a real world separation that is less than 100 percent complete. Each instance of the words "comprising," "comprises," and "comprise" in this patent document may be substituted with the phrases "consisting of," "consists of," and "consist of," respectively. The phrases "consisting essentially of," "consists essentially of," and "consist essentially of" refer to closed sets that optionally contain one or more undisclosed elements that do not materially affect the nature of any given closed set. For example, a product that consists essentially of a portion of a second lipid phase that is mechanically separated from a residual aqueous phase can nevertheless comprise an amount of the residual aqueous phase such as either (i) a trace amount, (ii) a fractional amount that cannot be removed in a viable commercial embodiment, or (iii) an amount that an unscrupulous patent infringer may intentionally include in an attempt to avoid a patent claim that matures from this patent document while performing a method that would otherwise infringe the patent claim. Each instance of the words "comprising," "comprises," and "comprise" in this patent document may be substituted with the phrases "consisting essentially of," "consists essentially of," and "consist essentially of," respectively. Each instance of the phrases "consisting of," "consists of," and "consist of" in this patent document may be substituted with the phrases "consisting essentially of," "consists essentially of," and "consist essentially of," respectively.

The following examples provide a framework to implement certain aspects of the disclosure, and these examples do not limit the scope of this patent document or any claim that matures from the disclosure of this patent document.

Example 1. Separating a Plurality of Cannabinoid Molecules and a Plurality of Second Molecules An industrial hemp extract is decarboxylated by vaporizing and condensing cannabinoids, terpenes, terpene alcohols, terpenoids, and other volatile molecules from the extract in approximately two seconds to produce a decarboxylated cannabinoid extract. This decarboxylation method is described in U.S. patent application Ser. No. 16/271,782, and it results in the recovery of cannabigerol, myrcene, and other thermolabile molecules that are not typically quantitatively recovered using conventional decarboxylation methods.

The decarboxylated cannabinoid extract comprises cannabidiol at a concentration of approximately 65 percent by mass, beta-caryophyllene at a concentration of approximately 5 percent by mass, tetrahydrocannabinol at a concentration of approximately 4 percent by mass, cannabichromene at a concentration of approximately 4 percent by mass, cannabigerol at a concentration of approximately 3 percent by mass, humulene at a concentration of approximately 3 percent by mass, and lesser concentrations of cannabidivarin, cannabigerovarin, tetrahydrocannabivarin, cannabichromevarin, cannabinol, bisabolol, guaiol, and linalool. The decarboxylated cannabinoid extract is then dissolved in ethanol to produce a starting composition. The starting composition has an ethoxide concentration that is greater than 2 nanomolar.

The starting composition is combined with a solubility-regulating composition that consists essentially of water to produce a heterogeneous composition that phase separates into an aqueous phase and a lipid phase. The solubility-regulating composition is added to the starting composition at a ratio such that both (i) each of the tetrahydrocannabinol, tetrahydrocannabivarin, cannabichromene, cannabichromevarin, cannabinol, beta-caryophyllene, humulene, bisabolol, guaiol, and linalool have a solubility in the aqueous phase that is less than 10 grams per liter such that greater than 65 percent of each of these ten molecules partition into the lipid phase, and (ii) each of the cannabidiol, cannabigerol, cannabidivarin, and cannabigerovarin have a solubility in the aqueous phase that is greater than 10 grams per liter such that greater than 65 percent of each of these four molecules remain in the aqueous phase of the heterogeneous composition. The aqueous phase has an ethoxide concentration that is both at least 0.2 nanomolar less than the ethoxide concentration of the starting composition and less than 95 percent of the ethoxide concentration of the starting composition.

The aqueous phase of the heterogeneous composition is separated from the lipid phase of the heterogeneous composition by sedimentation, filtering, or centrifugation to separate the cannabidiol, cannabigerol, cannabidivarin, and cannabigerovarin of the aqueous phase from the tetrahydrocannabinol, tetrahydrocannabivarin, cannabichromene, cannabichromevarin, cannabinol, beta-caryophyllene, humulene, bisabolol, guaiol, and linalool of the lipid phase. The aqueous phase is then aliquoted for use in subsequent examples.

Example 2. Producing a Cannabinoid Glass

A monosaccharide (such as glucose or fructose) is added to an aliquot of the aqueous phase of Example 1. The water and alcohol of the aliquot are then removed either in a rotary evaporator, in a vacuum oven, or by spray drying to produce a product. The product comprises cannabidiol at a concentration of greater than 80 percent by mass; cannabigerol at a concentration of greater than 2 percent by mass; cannabidivarin at a concentration greater than 0.3 percent by mass; and detectable cannabigerovarin. The product lacks each of tetrahydrocannabinol, tetrahydrocannabivarin, cannabichromene, cannabichromevarin, cannabinol, beta-caryophyllene, humulene, bisabolol, guaiol, and linalool at a concentration greater than 0.3 percent by mass. A cannabidiol crystal is added to an aliquot of the product; the aliquot is chilled at 0 degrees Celsius; and the aliquot does not crystallize, which confirms that the product is a glass.

Example 3. Producing Cannabinoid Crystals

The product of Example 2 is distilled using a short-path distillation apparatus to separate the molecules of the product based on boiling point and produce a purified product. The purified product comprises cannabidiol at a concentration of greater than 90 percent by mass; cannabigerol at a concentration of greater than 2 percent by mass; cannabidivarin at a concentration greater than 0.3 percent by mass; and detectable cannabigerovarin. The purified product lacks each of tetrahydrocannabinol, tetrahydrocannabivarin, cannabichromene, cannabichromevarin, cannabinol, beta-caryophyllene, humulene, bisabolol, guaiol, and linalool at a concentration greater than 0.3 percent by mass. The purified product spontaneously crystallizes at 21 degrees Celsius.

Example 4. Producing a Super-Cooled Cannabinoid Oil

A second solubility-regulating composition that consists essentially of water is added to an aliquot of the aqueous phase of Example 1 to produce a second heterogeneous composition comprising a second lipid phase and a residual aqueous phase. The second solubility-regulating composition is added to the aliquot at a ratio such that the cannabidiol, cannabigerol, cannabidivarin, and cannabigerovarin each have a solubility in the residual aqueous phase that is less than 10 grams per liter such that greater than 65 percent of each of these four molecules partition into the second lipid phase. The residual aqueous phase of the second heterogeneous composition is separated from the second lipid phase of the second heterogeneous composition at 21 degrees Celsius by sedimentation, filtering, or centrifugation to separate the cannabidiol, cannabigerol, cannabidivarin, and cannabigerovarin from the rest of the residual aqueous phase. The product is the separated second lipid phase, which is an oil that comprises cannabidiol at a concentration of greater than 85 percent by mass; cannabigerol at a concentration of greater than 2 percent by mass; cannabidivarin at a concentration greater than 0.3 percent by mass; and detectable cannabigerovarin. The product lacks each of tetrahydrocannabinol, tetrahydrocannabivarin, cannabichromene, cannabichromevarin, cannabinol, beta-caryophyllene, humulene, bisabolol, guaiol, and linalool at a concentration greater than 0.3 percent by mass. A cannabidiol crystal is added to an aliquot of the product at 21 degrees Celsius, and the aliquot crystallizes, which demonstrates that the product is a super-cooled oil because the freezing point of cannabidiol is significantly greater than 21 degrees Celsius.

Example 5. Producing a Cannabinoid Oil

A terpene, terpene alcohol, or terpenoid (such as beta-caryophyllene, humulene, bisabolol, guaiol, eucalyptol, limonene, linalool, myrcene, nerolidol, ocimene, pinene, and terpinolene) or a second cannabinoid (such as cannabidivarin, cannabigerol, cannabigerovarin, tetrahydrocannabivarin, cannabichromene, cannabichromevarin, or cannabinol) is added to the product of Example 4 to lower the freezing point of the cannabidiol and stabilize the oil against crystallization. A cannabidiol crystal is added to an aliquot of the stabilized product; the aliquot does not crystallize at 21 degrees Celsius; and the aliquot crystallizes at 0 degrees Celsius, which demonstrates that the product is a stable oil at 21 degrees Celsius.

What is claimed is:

1. A method to produce a cannabinoid glass from a decarboxylated cannabinoid extract, comprising:
combining (a) a starting composition comprising a decarboxylated cannabinoid extract and (b) a solubility-regulating composition to produce a heterogeneous composition, in which:
the starting composition comprises ethanol, a cannabinoid molecule, and a second molecule;
the cannabinoid molecule is cannabidiol, cannabidivarin, cannabigerol, or cannabigerovarin;
the second molecule is tetrahydrocannabinol, tetrahydrocannabivarin, or beta caryophyllene;
the ethanol is a solvent of the starting composition;
the cannabinoid molecule is a solute that is dissolved in the ethanol of the starting composition;
the second molecule is a solute that is dissolved in the ethanol of the starting composition;
the solubility-regulating composition comprises water;
the heterogeneous composition comprises an aqueous phase and a lipid phase;
the aqueous phase of the heterogeneous composition comprises at least 95 percent of the water of the heterogeneous composition;
the aqueous phase of the heterogeneous composition comprises at least 95 percent of the ethanol of the heterogeneous composition;
the second molecule has a solubility in the aqueous phase that is less than 10 grams per liter;
the lipid phase comprises greater than 65 percent of the second molecule of the heterogeneous composition;
the cannabinoid molecule has a solubility in the aqueous phase that is greater than 10 grams per liter; and
the aqueous phase comprises greater than 65 percent of the cannabinoid molecule of the heterogeneous composition;
(ii) separating the aqueous phase and the lipid phase to separate the cannabinoid molecule and the second molecule; and
(iii) separating the cannabinoid molecule from both (a) at least 95 percent of the water of the aqueous phase and (b) at least 95 percent of the ethanol of the aqueous phase to produce a product, in which:
the product consists essentially of the molecules of the aqueous phase that are separated from (a) the at least 95 percent of the water of the aqueous phase and (b) the at least 95 percent of the ethanol of the aqueous phase;
the product lacks the second molecule at a concentration greater than 0.3 percent by mass;
the cannabinoid molecule has a freezing point;
the product comprises a glass;
the glass comprises greater than 50 percent of the cannabinoid molecule of the product;
the glass comprises the cannabinoid molecule at a concentration greater than 50 percent by mass;
the glass has a glass-transition temperature that is less than the freezing point of cannabinoid molecule;
the glass lacks a freezing point; and
the glass lacks a melting point.

2. The method of claim 1, in which:
the decarboxylated cannabinoid extract is a decarboxylated full spectrum industrial hemp extract, a decarboxylated broad spectrum industrial hemp extract, or a decarboxylated industrial hemp distillate.

3. The method of claim 1, in which:
the decarboxylated cannabinoid extract comprises a plurality of cannabinoid molecules;
the plurality of cannabinoid molecules comprises two or more of cannabidiol, cannabidivarin, cannabigerol, and cannabigerovarin;
each cannabinoid molecule of the plurality of cannabinoid molecules is a solute that is dissolved in the ethanol of the starting composition;
each cannabinoid molecule of the plurality of cannabinoid molecules has a solubility in the aqueous phase that is greater than 10 grams per liter;
the aqueous phase comprises greater than 65 percent of each cannabinoid molecule of the plurality of cannabinoid molecules of the heterogeneous composition by mass; and
the product comprises each cannabinoid molecule of the plurality of cannabinoid molecules.

4. The method of claim 1, in which the cannabinoid molecule is cannabigerol, and the second molecule is beta-caryophyllene.

5. The method of claim 1, in which separating the aqueous phase and the lipid phase to separate the cannabinoid molecule and the second molecule comprises gravity-assisted sedimentation of the heterogeneous composition.

6. The method of claim 1, in which:
separating the cannabinoid molecule from both (a) the at least 95 percent of the water of the aqueous phase and (b) the at least 95 percent of the ethanol of the aqueous phase comprises combining the aqueous phase and a second solubility-regulating composition to (i) drive a portion of the cannabinoid molecule of the aqueous phase out of the aqueous phase and (ii) produce a second heterogeneous composition;
the second heterogeneous composition comprises a residual aqueous phase and a second lipid phase;
the residual aqueous phase is a liquid;
the residual aqueous phase comprises greater than 95 percent of the ethanol of the second heterogeneous composition;
the residual aqueous phase comprises greater than 95 percent of the water of the second heterogeneous composition;
the cannabinoid molecule of the second heterogeneous composition has a solubility in the residual aqueous phase that is less than 10 grams per liter;
the second lipid phase comprises greater than 80 percent of the cannabinoid molecule of the second heterogeneous composition;
the separation of the cannabinoid molecule from both (a) the at least 95 percent of the water of the aqueous phase and (b) the at least 95 percent of the ethanol of the aqueous phase further comprises mechanically separating the residual aqueous phase of the second heterogeneous composition from the second lipid phase of the second heterogeneous composition; and
the product consists essentially of the portion of the second lipid phase that is mechanically separated from the residual aqueous phase.

7. A method to produce cannabinoid crystals from a decarboxylated cannabinoid extract, comprising:

(i) combining (a) a starting composition comprising a decarboxylated cannabinoid extract and (b) a solubility-regulating composition to produce a heterogeneous composition, in which:
- the starting composition comprises ethanol, a cannabinoid molecule, and a second molecule;
- the cannabinoid molecule is cannabidiol, cannabidivarin, cannabigerol, or cannabigerovarin;
- the second molecule is tetrahydrocannabinol, tetrahydrocannabivarin, or beta caryophyllene;
- the ethanol is a solvent of the starting composition;
- the cannabinoid molecule is a solute that is dissolved in the ethanol of the starting composition;
- the second molecule is a solute that is dissolved in the ethanol of the starting composition;
- the solubility-regulating composition comprises water;
- the heterogeneous composition comprises an aqueous phase and a lipid phase;
- the aqueous phase of the heterogeneous composition comprises at least 95 percent of the water of the heterogeneous composition;
- the aqueous phase of the heterogeneous composition comprises at least 95 percent of the ethanol of the heterogeneous composition;
- the second molecule has a solubility in the aqueous phase that is less than 10 grams per liter;
- the lipid phase comprises greater than 65 percent of the second molecule of the heterogeneous composition;
- the cannabinoid molecule has a solubility in the aqueous phase that is greater than 10 grams per liter; and
- the aqueous phase comprises greater than 65 percent of the cannabinoid molecule of the heterogeneous composition;

(ii) separating the aqueous phase and the lipid phase to separate the cannabinoid molecule and the second molecule; and (iii) separating the cannabinoid molecule from both (a) at least 95 percent of the water of the aqueous phase and (b) at least 95 percent of the ethanol of the aqueous phase to produce a product, in which:
- the product consists essentially of the molecules of the aqueous phase that are separated from (a) the at least 95 percent of the water of the aqueous phase and (b) the at least 95 percent of the ethanol of the aqueous phase;
- the product lacks the second molecule at a concentration greater than 0.3 percent by mass;
- the product comprises crystals;
- the crystals comprise greater than 50 percent of the cannabinoid molecule of the product;
- the crystals comprise the cannabinoid molecule at a concentration greater than 50 percent by mass;
- the crystals have a melting point; and
- the crystals lack a glass-transition temperature.

8. The method of claim 7, further comprising dissolving the decarboxylated cannabinoid extract in the ethanol to produce the starting composition.

9. The method of claim 7, in which:
- the decarboxylated cannabinoid extract comprises a plurality of second molecules;
- the plurality of second molecules comprises two or more of tetrahydrocannabinol, tetrahydrocannabivarin, cannabichromene, cannabichromevarin, and cannabinol;
- each second molecule of the plurality of second molecules is a solute that is dissolved in the ethanol of the starting composition;
- each second molecule of the plurality of second molecules has a solubility in the aqueous phase that is less than 10 grams per liter;
- the lipid phase comprises greater than 65 percent of each second molecule of the plurality of second molecules of the heterogeneous composition by mass; and
- the product lacks each second molecule of the plurality of second molecules at a concentration greater than 0.3 percent by mass.

10. The method of claim 7, in which the cannabinoid molecule is cannabidiol, and the second molecule is tetrahydrocannabinol.

11. The method of claim 7, in which separating the aqueous phase and the lipid phase to separate the cannabinoid molecule and the second molecule comprises centrifuging the heterogeneous composition.

12. The method of claim 7, in which:
- separating the cannabinoid molecule from both (a) the at least 95 percent of the water of the aqueous phase and (b) the at least 95 percent of the ethanol of the aqueous phase comprises (i) vaporizing the at least 95 percent of the water to produce water vapor, (ii) vaporizing the at least 95 percent of the ethanol to produce ethanol vapor, and (iii) removing both the water vapor and the ethanol vapor from the aqueous phase using a vacuum;
- the vaporizing and removing are performed under conditions that do not vaporize and remove the cannabinoid molecule of the aqueous phase from the aqueous phase; and
- the product consists of the portion of the aqueous phase that is not both vaporized and removed from the aqueous phase.

13. The method of claim 7, in which separating the cannabinoid molecule from both (a) the at least 95 percent of the water of the aqueous phase and (b) the at least 95 percent of the ethanol of the aqueous phase comprises removing (a) the at least 95 percent of the water of the aqueous phase and (b) the at least 95 percent of the ethanol of the aqueous phase under vacuum either in a rotary evaporator, in a vacuum oven, or by lyophilization.

14. A method to produce a supercooled cannabinoid oil from a decarboxylated cannabinoid extract, comprising:
(i) combining (a) a starting composition comprising a decarboxylated cannabinoid extract and (b) a solubility-regulating composition to produce a heterogeneous composition, in which:
- the starting composition comprises ethanol, a cannabinoid molecule, and a second molecule;
- the cannabinoid molecule is cannabidiol, cannabidivarin, cannabigerol, or cannabigerovarin;
- the second molecule is tetrahydrocannabinol, tetrahydrocannabivarin, or beta caryophyllene;
- the ethanol is a solvent of the starting composition;
- the cannabinoid molecule is a solute that is dissolved in the ethanol of the starting composition;
- the second molecule is a solute that is dissolved in the ethanol of the starting composition;
- the solubility-regulating composition comprises water;
- the heterogeneous composition comprises an aqueous phase and a lipid phase;
- the aqueous phase of the heterogeneous composition comprises at least 95 percent of the water of the heterogeneous composition;
- the aqueous phase of the heterogeneous composition comprises at least 95 percent of the ethanol of the heterogeneous composition;

the second molecule has a solubility in the aqueous phase that is less than 10 grams per liter;

the lipid phase comprises greater than 65 percent of the second molecule of the heterogeneous composition;

the cannabinoid molecule has a solubility in the aqueous phase that is greater than 10 grams per liter; and the aqueous phase comprises greater than 65 percent of the cannabinoid molecule of the heterogeneous composition;

(ii) separating the aqueous phase and the lipid phase to separate the cannabinoid molecule and the second molecule; and (iii) separating the cannabinoid molecule from both (a) at least 95 percent of the water of the aqueous phase and (b) at least 95 percent of the ethanol of the aqueous phase to produce a product, in which:

the product consists essentially of the molecules of the aqueous phase that are separated from (a) the at least 95 percent of the water of the aqueous phase and (b) the at least 95 percent of the ethanol of the aqueous phase;

the product lacks the second molecule at a concentration greater than 0.3 percent by mass;

the product comprises an oil;

the oil comprises greater than 50 percent of the cannabinoid molecule of the product;

the oil comprises the cannabinoid molecule at a concentration greater than 50 percent by mass;

the oil is a supercooled liquid;

the oil has a freezing point; and the oil lacks a glass-transition temperature.

15. The method of claim 14, further comprising heating a cannabinoid extract to decarboxylate the cannabinoid extract and produce the decarboxylated cannabinoid extract.

16. The method of claim 14, in which:

the decarboxylated cannabinoid extract comprises a plurality of second molecules;

the plurality of second molecules comprises two or more of beta-caryophyllene, bisabolol, eucalyptol, guaiol, humulene, limonene, myrcene, nerolidol, ocimene, pinene, terpinolene, and linalool;

each second molecule of the plurality of second molecules is a solute that is dissolved in the ethanol of the starting composition;

each second molecule of the plurality of second molecules has a solubility in the aqueous phase that is less than 10 grams per liter;

the lipid phase comprises greater than 65 percent of each second molecule of the plurality of second molecules of the heterogeneous composition by mass; and the product lacks each second molecule of the plurality of second molecules at a concentration greater than 0.3 percent by mass.

17. The method of claim 14, in which the cannabinoid molecule is cannabidivarin, and the second molecule is tetrahydrocannabivarin.

18. The method of claim 14, in which separating the aqueous phase and the lipid phase to separate the cannabinoid molecule and the second molecule comprises filtering the heterogeneous composition.

19. The method of claim 14, in which separating the cannabinoid molecule from both (a) the at least 95 percent of the water of the aqueous phase and (b) the at least 95 percent of the ethanol of the aqueous phase comprises spray drying the aqueous phase.

20. A method to separate cannabidiol and tetrahydrocannabinol, comprising:

(i) providing a starting composition comprising ethanol, cannabidiol, and tetrahydrocannabinol, in which:

the starting composition comprises an alcohol phase;

the alcohol phase is a liquid;

the alcohol phase comprises (a) at least 90 percent of the ethanol of the starting composition, (b) at least 50 percent of the cannabidiol of the starting composition, and (c) at least some of the tetrahydrocannabinol of the starting composition;

the ethanol of the alcohol phase is a solvent;

the cannabidiol of the alcohol phase is a solute that is dissolved in the ethanol of the alcohol phase;

the tetrahydrocannabinol of the alcohol phase is a solute that is dissolved in the ethanol of the alcohol phase;

the ethanol of the alcohol phase is present in the alcohol phase at a concentration of at least 35 percent and no greater than 99 percent by mass;

the starting composition comprises the cannabidiol at a concentration of at least 0.65 percent and no greater than 65 percent by mass;

the starting composition comprises the tetrahydrocannabinol at a concentration of at least 0.065 percent by mass;

the starting composition comprises the cannabidiol and the tetrahydrocannabinol at a cannabidiol-to-tetrahydrocannabinol ratio of less than 350:1 by mass;

the cannabidiol of the starting composition has a solubility in the alcohol phase that is greater than 10 grams per liter; and the tetrahydrocannabinol of the starting composition has a solubility in the alcohol phase that is greater than 10 grams per liter;

(ii) decreasing the solubility of the tetrahydrocannabinol in the alcohol phase of the starting composition by combining the alcohol phase and a solubility-regulating composition to (a) drive a portion of the tetrahydrocannabinol of the alcohol phase out of the alcohol phase and (b) produce a heterogeneous composition, in which:

the solubility-regulating composition comprises water;

the solubility-regulating composition comprises the water at a concentration by mass that is greater than the concentration by mass of any water that is present in the alcohol phase of the starting composition such that the combination of the alcohol phase and the solubility-regulating composition has a greater concentration of water than the alcohol phase of the starting composition;

the heterogeneous composition comprises each of (a) the ethanol of the starting composition, (b) the cannabidiol of the starting composition, (c) the tetrahydrocannabinol of the starting composition, and (d) the water of the solubility-regulating composition;

the heterogeneous composition comprises an aqueous phase and a tetrahydrocannabinol-enriched lipid phase;

the aqueous phase is a liquid;

the aqueous phase comprises greater than 50 percent of the cannabidiol of the heterogeneous composition;

the aqueous phase comprises greater than 50 percent of the ethanol of the heterogeneous composition;

the aqueous phase comprises at least 95 percent of the water of the heterogeneous composition;

either (a) the ethanol of the aqueous phase is a solvent, and the water of the aqueous phase is a solute that is dissolved in the ethanol of the aqueous phase, or (b)

the water of the aqueous phase is a solvent, and the ethanol of the aqueous phase is a cosolvent;

the cannabidiol of the heterogeneous composition has a solubility in the aqueous phase that is greater than 10 grams per liter;

the cannabidiol of the aqueous phase is a solute that is dissolved in the solvent of the aqueous phase;

the tetrahydrocannabinol of the heterogeneous composition has a solubility in the aqueous phase that is less than 10 grams per liter;

the aqueous phase comprises the cannabidiol of the aqueous phase and any tetrahydrocannabinol that is dissolved in the solvent of the aqueous phase at a cannabidiol-to-tetrahydrocannabinol ratio that is greater than 350:1 by mass; and the tetrahydrocannabinol-enriched lipid phase comprises greater than 50 percent of the tetrahydrocannabinol of the heterogeneous composition;

(iii) selecting either a fraction or all of the heterogeneous composition for further processing to produce a fractionated heterogeneous composition, in which:

the fractionated heterogeneous composition comprises a fractionated aqueous phase and a fractionated tetrahydrocannabinol-enriched lipid phase;

the fractionated aqueous phase consists of either a fraction or all of the aqueous phase of the heterogeneous composition;

the fractionated aqueous phase comprises either a fraction or all of the cannabidiol of the aqueous phase;

the fractionated aqueous phase comprises either a fraction or all of the ethanol of the aqueous phase;

the fractionated aqueous phase comprises either a fraction or all of the water of the aqueous phase;

the fractionated tetrahydrocannabinol-enriched lipid phase consists of either a fraction or all of the tetrahydrocannabinol-enriched lipid phase of the heterogeneous composition; and the fractionated tetrahydrocannabinol-enriched lipid phase comprises either a fraction or all of the tetrahydrocannabinol of the tetrahydrocannabinol-enriched lipid phase of the heterogeneous composition;

(iv) mechanically separating the fractionated aqueous phase of the fractionated heterogeneous composition from the fractionated tetrahydrocannabinol-enriched lipid phase of the fractionated heterogeneous composition to mechanically separate the cannabidiol of the fractionated aqueous phase from the tetrahydrocannabinol of the fractionated tetrahydrocannabinol-enriched lipid phase;

(v) selecting either a fraction or all of the fractionated aqueous phase for further processing to produce a second fractionated aqueous phase, in which:

the second fractionated aqueous phase comprises either a fraction or all of the cannabidiol of the fractionated aqueous phase;

the second fractionated aqueous phase comprises either a fraction or all of the ethanol of the fractionated aqueous phase; and the second fractionated aqueous phase comprises either a fraction or all of the water of the fractionated aqueous phase;

(vi) separating (a) a majority of the ethanol of the second fractionated aqueous phase and a majority of the water of the second fractionated aqueous phase from (b) a majority of the cannabidiol of the second fractionated aqueous phase to produce a product, in which:

the product comprises cannabidiol;

the product lacks tetrahydrocannabinol at a concentration greater than 0.3 percent by mass;

the product comprises cannabidiol and any tetrahydrocannabinol at a cannabidiol-to tetrahydrocannabinol ratio that is greater that 350:1 by mass;

the product lacks ethanol at a concentration greater than 5 percent by mass; and the product lacks water at a concentration greater than 5 percent by mass.

* * * * *